(12) United States Patent
Hwang et al.

(10) Patent No.: US 7,238,505 B2
(45) Date of Patent: Jul. 3, 2007

(54) IMMOBILIZED DNA POLYMERASE

(75) Inventors: Hyun Jin Hwang, Seoul (KR); Jeong Hee Kim, Seoul (KR)

(73) Assignee: Ahram Biosystems Inc., Seoul (KR)

( * ) Notice: Subject to any disclaimer, the term of this patent is extended or adjusted under 35 U.S.C. 154(b) by 213 days.

(21) Appl. No.: 10/406,154

(22) Filed: Apr. 2, 2003

(65) Prior Publication Data

US 2004/0086889 A1    May 6, 2004

Related U.S. Application Data

(63) Continuation-in-part of application No. PCT/KR01/01650, filed on Sep. 29, 2001, and a continuation-in-part of application No. PCT/KR01/01239, filed on Jul. 20, 2001, and a continuation-in-part of application No. PCT/KR00/01104, filed on Oct. 4, 2000.

(60) Provisional application No. 60/369,512, filed on Apr. 2, 2002.

(30) Foreign Application Priority Data

Oct. 4, 2000   (KR) .................... 00/01104
Jul. 20, 2001  (KR) .................... 01/01239

(51) Int. Cl.
    C12N 11/08   (2006.01)
    C12N 11/02   (2006.01)
    C12N 11/10   (2006.01)
    C12Q 1/68    (2006.01)
    C07H 21/00   (2006.01)

(52) U.S. Cl. .................... 435/180; 435/6; 435/177; 435/178; 536/22.1

(58) Field of Classification Search .................... None
    See application file for complete search history.

(56) References Cited

U.S. PATENT DOCUMENTS

| 4,180,383 A | 12/1979 | Johnson ................ 422/69 |
| 6,096,499 A * | 8/2000 | Kozlowski et al. .......... 435/6 |
| 6,172,202 B1 | 1/2001 | Marcucci et al. .......... 530/406 |
| 6,194,552 B1 | 2/2001 | Velander et al. .......... 530/413 |
| 6,610,479 B1 * | 8/2003 | Lundeberg et al. .......... 435/6 |

FOREIGN PATENT DOCUMENTS

| WO | WO 94/13322 | 6/1994 |
| WO | WO 02/04483 A1 | 1/2002 |
| WO | WO 02/29027 A1 | 4/2002 |

OTHER PUBLICATIONS

Subramanian, et al., "Effect of Antibody Orientation on Immunosorbent Performance"; Journal of Molecular Recognition, vol. 9, pp. 528-535, 1996.

* cited by examiner

*Primary Examiner*—David M. Naff
(74) *Attorney, Agent, or Firm*—JHK Law; Joseph Hyosuk Kim

(57) ABSTRACT

The present invention relates to a DNA polymerase immobilized by covalent bonding. More particularly, the present invention relates to an immobilized DNA polymerase whose activity is maximally preserved by masking the active site of the DNA polymerase and optimizing interaction of the masked molecule to the substrate material. In one embodiment, the average activity of the immobilized DNA polymerase is more than about 10% relative to that of the solution phase DNA polymerase. Further provided by the invention are methods and kits for performing polymerase chain reactions (PCR).

16 Claims, 9 Drawing Sheets

IMMOBILIZED DNA POLYMERASE

CROSS-REFERENCE TO RELATED APPLICATIONS

The present application is a continuation-in-part of PCT/KR01/01650 as filed on Sep. 29, 2001 which application claims the benefit of PCT/KR00/01104 filed on Oct. 4, 2000 and PCT/KR01/01239 filed on Jul. 20, 2001. The CIP application claims further priority to U.S. Provisional Application Ser. No. 60/369,512 as filed on Apr. 2, 2002. The disclosures of PCT/KR00/01104; PCT/KR01/01239; PCT/KR01/01650; and Ser. No. 60/369,512 are incorporated herein by reference.

TECHNICAL FIELD

The present invention relates to a DNA polymerase immobilized by covalent bonding. More particularly, the present invention relates to an immobilized DNA polymerase whose activity is maximally preserved by masking the active site of the DNA polymerase and optimizing interaction of the masked molecule to the substrate material. In one embodiment, the average activity of the immobilized DNA polymerase is more than about 10% relative to that of the solution phase DNA polymerase.

BACKGROUND

Enzymes are proteins that catalyze chemical reactions in vivo, and they have very specific catalytic activities toward chemical reaction and substrate. Enzyme reactions using their specific catalytic activities are utilized in medical and life science research. Enzymes find use in various catalytic chemical processes as well. In these utilizations of enzyme reactions, it is required in many cases to separate enzymes from reaction solutions after the reactions are completed, for the purpose of purifying products or recycling the enzymes. However, in solution phase, it takes long time and is very cumbersome to separate and purify materials such as enzymes and reaction products from reaction samples. Therefore, it is very important in the utilization of enzyme reactions to develop a method of simplifying the enzyme separation process.

Since immobilized enzymes can provide very efficient methods to simplify the enzyme separation process, a variety of work has been performed extensively on the development of methods for immobilizing enzymes. The "immobilized enzyme" as used herein means an enzyme that is physically or chemically bound to a substrate material while retaining substantial catalytic activity. Advantages of using such immobilized enzymes are as follows.

For instance, the purification or separation process of reaction samples can be simplified since the immobilized enzyme can be easily separated and recycled from reaction samples by simply removing the immobilized enzyme after an enzyme reaction. Also, the cost can be reduced by reusing the recycled immobilized enzyme. In addition, because multiple processes where enzyme reactions are included can be simplified, the efficiency of the overall reaction processes can be increased. Further, the efficiency of utilizing enzyme can be increased due to additional effects such as an enhancement in physical stability of enzyme after immobilization or a change in the conditions of enzyme reaction.

Examples of the enzyme immobilization methods include the carrier-binding method where enzymes bind to a carrier that is typically insoluble to water, the crosslinking method where enzymes are connected one another using a reagent having multiple reaction groups, and the entrapping method where enzymes are surrounded by semi-permeable gel or macromolecular membrane. The immobilized DNA polymerase in the present invention is prepared by a kind of the carrier-binding method where enzymes are immobilized on a substrate material with covalent bonding. The characteristics of the carrier-binding method are thus described in detail below.

In the carrier-binding method, the kind of a carrier and the method of binding are selected based on physical and chemical interactions between the enzyme and the carrier. This is because the amount and the characteristics of the enzyme after immobilization on the carrier depend greatly on the characteristics of the carrier and the method of binding. This method is thus classified according to the method of binding between the enzyme and the carrier, and examples of the carrier-binding method include the physical adsorption method via hydrogen bonding and Van der Waals interaction, the ionic bonding method where an enzyme binds to a polysaccharide having ion exchange groups or a synthetic macromolecule via ionic bonding, and the covalent bonding method where covalent bonding is formed between an enzyme and a carrier.

The physical adsorption method or the ionic bonding method has an advantage that the possibility of damaging the enzyme activity by immobilization bonding is low, since the enzyme binding process to a carrier is relatively simple and the influence on the active site structure of the enzyme is relatively low due to weak binding. However, there is a disadvantage that the enzyme can be lost even with the small change in temperature and pH, due to the weak binding between the enzyme and the carrier, and the low specificity that causes nonspecific binding of undesired proteins.

The disadvantage of the above two method can be solved in the covalent bonding method, since in the covalent bonding method, enzymes are immobilized by forming a strong bond between the enzyme and the carrier. Therefore, works on a variety of the covalent bonding methods have been performed using various kinds of carriers.

Since the enzyme has various reaction groups that can form covalent bond with a carrier, for example, amine, carboxyl, hydroxyl, thiol, imidazole, etc., immobilization reactions toward such reaction groups that can be performed in aqueous solution have been developed such as amide bond formation reaction, alkylation or arylation, disulfide bond formation, diazotization, etc. In addition, there has been reported an immobilization method where an immobilization reaction group on a substrate material reacts directly with a reaction group of an enzyme, or an immobilization method where a substrate material and an enzyme are connected using a linker having reaction groups at both ends. However, the covalent bonding method has a difficulty of preserving the enzyme activity after immobilization, since a strong bond formed between the enzyme and the carrier gives rise to the structural change in the enzyme which in turn increases the possibility of damaging the enzyme activity.

The most important point in immobilizing an enzyme on a substrate material with covalent bonding is that the damage of the enzyme activity due to a structural change in the enzyme active site by immobilization bonding must be prevented. Therefore, it is essential that the immobilization reaction must not occur at or near the active site. And also, even if the immobilization reaction occurs at a site distant from the active site of the enzyme, the allosteric effect that eventually reduces the enzyme activity by influencing the total structure of the enzyme must not occur. Therefore, in order to immobilize the enzyme with its activity preserved, it must be possible to select an immobilization site in the enzyme toward which immobilization bonding occurs, i.e., to select a reaction group of the enzyme located at a particular site such that the activity is not damaged after the immobilization bonding. In other words, an oriented immobilization should be possible wherein the enzyme can be immobilized in an oriented manner so that a reaction group of the enzyme located at the particular site forms an immobilization bonding. However, an enzyme is a macromolecule that has a great number of amino acids connected by amide bonding. Due to such characteristic of the enzyme, reaction groups available for immobilization reaction, for example, amine, carboxyl, hydroxyls, etc. are numerous and they are distributed throughout the enzyme. Therefore, it is impossible with the prior technologies developed to date to direct an oriented immobilization by selecting a reaction group of an enzyme located at a particular site. In other words, in the enzyme immobilization using the prior art immobilization methods, random immobilization reactions occur toward a plurality of reaction groups in the enzyme. Therefore, an immobilization bonding can be formed at an undesirable site or a plurality of immobilization bonding can be formed, thereby severely damaging the enzyme activity.

In addition to the damage in the enzyme activity due to the nonspecific nature of the immobilization reaction in the prior art immobilization methods, the formation of covalent bonding by itself can possibly reduce the enzyme activity largely because it requires rearrangement of electrons. That is, even if it is possible to select a reaction group of the enzyme located at a particular site so as to direct an oriented immobilization toward the reaction group, it is impossible to confirm presence of the covalently immobilized enzyme with its activity preserved without damage unless an oriented immobilization is actually performed.

There have been efforts to immobilize certain biomolecules other than DNA polymerase. For example, U.S. Pat. No. 4,180,383 discloses a method of making an immobilized immunoadsorbent in which an antigen is used as a masking agent to protect (mask) an antibody of interest before reaction with a polymer support. U.S. Pat. No. 6,194,552 and Subramanian A. and W. Velander (1996) *J. of Mol. Recognition* 9: 528 also disclose a similar method for preparing an immobilized immunoadsorbent using an antigen as a masking agent. U.S. Pat. No. 6,172,202 (see also PCT/EP93/03429 (WO 94/13322) discloses a method for preparing a conjugate of a protein (or a glycoprotein) with a water soluble protein using an antibody or an antiidiotypic antibody as a masking agent.

However, there is general understanding that such methods work largely because antibodies are robust molecules. That is, even unmasked antibodies are thought to be less sensitive to conformational changes induced by immobilization reactions occurring outside the antigen binding pocket. In marked contrast, DNA polymerase is thought to be especially sensitive to reactions involving amino acid residues within and outside the catalytic site. In particular, the prolonged antigen binding conditions required by the prior masking procedures are believed to be particularly unsuitable for manipulating sensitive DNA polymerases.

More generally, there is increasing recognition that prior methods of protecting antibodies and certain proteins before reaction with a substrate material will not provide good results with DNA polymerases. There is doubt that current approaches that focus on protecting active sites will be insufficient to preserve the biological activity of a DNA polymerase following immobilization. In practice, it has been difficult or in some cases impossible to preserve the biological activity of DNA polymerase after an immobilization procedure.

It would be desirable to have a method of immobilizing a DNA polymerase to a substrate material. It would be further desirable to have methods that protect not only the catalytic site of the DNA polymerase but also optimize interaction of the enzyme with the substrate material.

SUMMARY OF INVENTION

The present invention features a method for immobilizing a DNA polymerase to a substrate material. The method is broadly applicable to preserving the biological activity of the enzyme after immobilization on one or a combination of different substrate materials. Preferred invention methods protect (mask) the active site of the DNA polymerase and suitably optimize interaction of the masked enzyme to the substrate.

It has been found that it is possible to preserve the biological activity of a DNA polymerase on a wide variety of substrate materials by masking the active site and optimizing interaction of the masked molecule to the substrate material of interest. More specifically, it has been discovered that by controlling the rate of immobilization of the masked DNA polymerase to the substrate material, it is possible to preserve a substantial fraction of the solution activity of the enzyme following immobilization to the substrate material. In preferred embodiments, the rate of the immobilization reaction is optimized so as to minimize the number of immobilization bonds formed between each masked DNA polymerase and the substrate material and at the same time to maximize the probability of immobilizing the molecule to the greatest extent possible. Surprisingly, it has been discovered that by controlling and thus optimizing the rate of the immobilization reaction under conditions in which formation of multiple immobilization bonding for each immobilized molecule is substantially reduced or eliminated and overall number density of the immobilized (masked) molecule is enhanced, more than about 10% of the natural biological activity of the subject molecule can be retained, preferably more than about 20%, 30%, 50% or more of such activity when compared to activity obtained in solution.

As will be more apparent from the discussion and Examples that follow, Applicants have learned that it is possible to optimize the rate of the immobilization reaction by balancing two competing kinetic parameters in the immobilization reaction. This inventive concept can be appreciated by considering a hypothetical (ideal) immobilization reaction where it would be possible to achieve a theoretical maximum value of the preserved activity per unit area of immobilization on the substrate material if the following two conditions could be fulfilled simultaneously: (1) forming a minimum number of immobilization bonding per biologically active molecule so as not to reduce or eliminate activity of the immobilized molecule and (2) forming a maximum number density of the DNA polymerase molecules at which no or negligible activity reducing effect occurs. However in "real life" immobilization reactions involving DNA polymerases, satisfying these two conditions have been difficult or sometimes impossible because they oppose each other. That is, while the rate of the immobilization reaction must be reduced to reduce the number of the immobilization bonding per immobilized DNA polymerase, the rate must also be enhanced to increase the number of immobilized molecules.

It is an object of the present invention to provide a solution to this thermodynamic dilemma by identifying a "compromise" or "opportunity window" between the two opposing kinetic parameters. That is, the invention provides specific reaction parameters that optimize both opposing kinetic parameters and allow one to immobilize nearly one or a combination of different DNA polymerases or fragments thereof with a highly preserved activity. In preferred embodiments, the immobilized molecule has a kinetically allowed maximum activity per unit area of immobilization on the substrate material.

More specifically, it is a goal of the present invention to provide optimized immobilization reaction conditions that can be characterized as providing: 1) maximum preservation of activity of individual DNA polymerase molecules, 2) minimal probability of forming multiple immobilization bonds per immobilized molecule and 3) maximal increase in overall number density of the immobilized DNA polymerase molecule (i.e., by maximizing the probability of forming at least one bond per each enzyme molecule, within the practical limit). The Examples below show a preferred procedure in which the two opposing kinetic parameters discussed above can be nearly independently controlled or optimized. If desired, the procedure can be readily adapted in accord with this invention to immobilize nearly any type of DNA polymerase (e.g., from animal, plant, microbial or fungal source) or fragment thereof in instances where significant preservation of bioactivity in bound form is needed such as in a Polymerase Chain Reaction (PCR) or related protocol.

It will be apparent that the number of the immobilization bonds per immobilized molecule will often depend more on the number density (and also reactivity) of the reaction group on the substrate material than many other kinetic parameters mentioned herein. By the phrase "number density" is meant the number of entities of interest present per unit area of a surface. For example, the number density of the reaction group on the supporting material means the number of the reaction groups per unit area of the surface of the supporting material. Without wishing to be bound to theory, it is believed that when a molecule is bound to the substrate material by formation of first immobilization bond, formation or additional bonds between the plurality of the reaction groups on the bound molecule and the plurality of the reaction groups on the supporting material becomes "intramolecular". That binding is generally understood to be much faster than "intermolecular" macroscopic kinetics between the not-yet-bound DNA polymerase molecules and the substrate material. The invention provides a solution to this problem, for instance, by providing control over other reaction parameters such as concentration of the enzyme, the reaction time, temperature, pH, and optionally a reaction inducing agent such as a coupling agent to increase the overall number density of the immobilized molecule. Preferably, the number of the immobilization bonds per immobilized molecule is minimized by controlling (typically reducing) the number density of the reaction group on the substrate material. Surprisingly, it has been discovered that by controlling and thus optimizing the rate of the immobilization reaction, more than about 10% of the natural biological activity of the subject molecule can be retained, typically more than about 20%, 30% or 40% of such activity as compared to the theoretical maximum activity per unit area of immobilization on the substrate material (i.e., compared to the full monolayer amount of immobilized, fully active molecules).

The present invention addresses this need by providing, for the first time, a reliable and generally applicable method of preserving the biological activity of a wide range of DNA polymerases and biologically active fragments thereof. Such molecules include DNA polymerases and fragments thereof isolated or derived from animal cells, plant cells, bacterial cells, virally infected plant and animal cells, thermophilic bacteria, fungi etc. Preferred practice of the invention involves masking the active site(s) of the enzyme, usually with a suitable enzyme substrate such as nucleic acid molecule, and controllably optimizing the rate of immobilization of the masked molecule to the substrate material. Preferably, the rate of immobilization is adjusted such that a minimum number of immobilization bonds are formed per immobilized molecule and at the same time a maximum amount of the masked molecule is bound to the substrate material within the practical limit. Importantly, it has been found that the masking and controlled immobilization steps act synergistically to preserve the biological activity of a wide range of important molecules. That is, the observed activity of a biologically active molecule immobilized according to the invention is surprisingly higher and more robust when compared to results obtained by only masking the molecule or controlling the rate of immobilization of an unmasked molecule.

Without wishing to be bound to theory, it is believed that prior methods of masking certain biologically active molecules have relied too much on protecting active sites. This approach, while affording some protection against harmful immobilization reactions, is believed to have left significant portions of many molecules exposed. For instance, regions outside the catalytic site of a DNA polymerase (accessory or non-catalytic sites) could be exposed to harmful reaction with the substrate material. There is increasing acknowledgement that non-catalytic sites of many DNA polymerases can impact catalysis. Prior to the present invention, there has been no reliable and broadly applicable way of protecting the catalytic and accessory sites of DNA polymerase from undesired reaction with the substrate material. This drawback has hindered research and medical efforts, particularly those efforts that rely on PCR and related procedures.

The present invention addresses this need by providing a reliable and generally applicable method of preserving the activity of DNA polymerase including catalytically active fragments thereof (e.g., Klenow fragment). Preferred practice of the invention involves masking the active site of the DNA polymerase and controllably optimizing the rate of immobilization of the masked molecule to the substrate material. Preferably, the rate of immobilization is adjusted such that a minimal number of immobilization bonds are formed per immobilized molecule and at the same time a maximum amount of the masked molecule is bound to the substrate material within the practical limit. Importantly, it has been found that the masking and controlled immobilization steps act synergistically to preserve the catalytic activity of the immobilized DNA polymerase or catalytically active fragment. Immobilization results achieved with the invention are also significantly higher when compared to more traditional random immobilization approaches e.g., by at least about 10-fold or more.

As will be discussed below, successful practice of the invention can be achieved by performing one or a combination of protection strategies. For instance, the rate of immobilization of the masked molecule to a desired substrate material can be controlled by changing the number density and/or the reactivity (or the reaction lifetime) of the reaction group on the substrate material. Typically the number density of the reaction group on the substrate material is substantially lower (about 5 to about 100 fold lower) than those of the prior substrate materials. If the reactivity (or the reaction lifetime) of the reaction group is higher (lower), the number density of same should be controlled to a lower (higher) density. The number density and the reactivity of the reaction group are closely related to the number of immobilization bonds formed per immobilized molecule. Therefore, these parameters should be substantially reduced to reduce or avoid formation of multiple immobilization bonds per each immobilized molecule that is harmful for preserving catalytic activity of the DNA polymerase after immobilization. In embodiments in which a linking group is used to join the enzyme to the substrate material, the number density and the reactivity of the linking group or a portion thereof is controlled and preferably substantially reduced. Other strategies for controlling the rate of immobilization of the masked molecule to the substrate material include adjusting one or more of the concentration or the molar amount of the masked molecule to be bound, pH, reaction time, reaction temperature, and type of linking group(s) and coupling reagent(s) used. A particular strategy for controlling the rate of immobilization of a masked molecule can be practiced alone or in combination with at least one other of these specific reaction rate control strategies.

Practice of the invention provides important advantages.

For example, preferred use of the invention helps to orient the DNA polymerase such that the catalytic site is spared unnecessary chemical reaction. That is, masking the DNA polymerase with a suitable reactant (generally DNA or an acceptable derivative thereof) helps to focus immobilization reactions away from the catalytic site. Additionally, by controlling the rate of immobilization in accord with the invention, covalent bonding to sensitive DNA polymerases or catalytically active fragments thereof can be kept to a minimum while, at the same time, permitting some covalent bonding to immobilize the enzyme or fragment. As discussed below, it has been found that the average number of covalent bonds between the masked DNA polymerase and the substrate material is typically less than about 10, preferably less than about 5 and more preferably between about 1 to 2 with about 1 being most preferred for most applications.

A DNA polymerase immobilized in accord with the present invention can be used extensively in a variety of nucleic acid amplification technologies that use the polymerase chain reaction (PCR) and also in the DNA recombination processes in the field of genetic engineering for the purpose of research and development and clinical diagnosis. However, an immobilized DNA polymerase whose activity for DNA polymerization is preserved to be high enough to use in the DNA recombination processes and the PCR amplification technology has heretobefore not been provided.

Accordingly, it is an objective of the present invention to provide an immobilized DNA polymerase that is immobilized via covalent bonding and whose activity is highly preserved.

More particularly, it is an objective of the present invention to provide an immobilized DNA polymerase whose average activity is preserved higher than about 10% relative to that of a solution phase DNA polymerase. This will be achieved, in one embodiment, by making it possible that the immobilization site in the enzyme where a linker binds is selected such that the DNA polymerase is oriented for immobilization bonding, and also the average number of covalent bonding per immobilized DNA polymerase is controllably reduced, while the DNA polymerase is immobilized via covalent bonding.

It is another objective of the present invention to provide an immobilized DNA polymerase in which a DNA substrate is bound to mask the active site.

It is still another objective of the present invention to provide an immobilized DNA polymerase that can be easily separated, recycled, and reused, by providing the immobilized DNA polymerase and the immobilized DNA polymerase whose active site is masked.

The person skilled in the art of the present invention can easily recognize other objectives and advantages from the drawings and the detailed description of the present invention.

In order to achieve the objectives, the present invention provides a novel immobilized DNA polymerase with highly preserved activity that is immobilized via covalent bonding.

More particularly, the present invention provides an immobilized DNA polymerase comprising a DNA polymerase, a linker, and a substrate material, wherein the DNA polymerase forms covalent bonding with at least one linker; the linker forms chemical bonding with the substrate material; the immobilization site of the DNA polymerase that is connected to the linker is selected such that the DNA polymerase is oriented; and the average number of covalent bonds per immobilized DNA polymerase is controlled, such that the average activity of the immobilized DNA polymerase is preserved more than about 10% relative to that of the solution phase DNA polymerase.

The present invention further provides an immobilized DNA polymerase comprising a DNA polymerase, whose active site is masked with a DNA substrate, a linker, and a substrate material, wherein the DNA polymerase forms covalent bonding with at least one linker; the linker forms chemical bonding with the substrate material; the immobilization site of the DNA polymerase that is connected to the linker is selected such that the DNA polymerase is oriented; and the average number of covalent bonding per immobilized DNA polymerase is controlled, such that the average activity of the immobilized DNA polymerase after demasking the DNA substrate is preserved more than about 10% relative to that of the solution phase DNA polymerase.

The most important point in immobilizing an enzyme on a substrate material with covalent bonding is that the damage of the enzyme activity due to a structural change in the enzyme active site by immobilization bonding must be prevented. In the random immobilization methods of the prior art that can provide a covalently immobilized enzyme, it is almost impossible to preserve the activity of an enzyme after immobilization, since covalent bonding can be formed at or near the active site of the enzyme and an allosteric effect which eventually reduces or damages the enzyme activity can take place even if immobilization bonding is formed at a site distant from the active site.

The immobilized DNA polymerase provided by the present invention has highly preserved activity, given the following characteristics for covalently immobilizing the DNA polymerase on the substrate material through the linker.

For instance, in the present invention, an oriented immobilization is induced to form covalent bonding for immobilization at a site distant from the active site of the DNA polymerase so that the activity of the enzyme is preserved after covalent immobilization. In order for the oriented immobilization to occur, the DNA polymerase is masked by a DNA substrate that selectively binds to the active site of the DNA polymerase. In this manner, formation of covalent bonding for immobilization at or near the active site of the DNA polymerase is prevented. In the case where the DNA polymerase is immobilized in the same way as described above but without masking the enzyme, that is, the case where a random immobilization takes place, it is confirmed that the activity is almost lost after immobilization. This confirms that an oriented immobilization occurs when the enzyme is masked.

In addition, in the present invention of covalently immobilizing the DNA polymerase, immobilization conditions are optimized to achieve high activity of the immobilized DNA polymerase. In order to control the immobilization conditions, concentration (or number density) of an immobilization reaction group on the substrate material that forms a covalent immobilization bond with the DNA polymerase, is controlled by changing the concentration of the linker that is chemically bound to the substrate material. In order to achieve high activity of the immobilized DNA polymerase, (1) the number of immobilized DNA polymerases per unit area of the substrate material should be high, (2) the number of covalent bonding for immobilization per immobilized DNA polymerase should be most preferably one, or else it should be maintained as minimal as possible, to the extent that the active site of the immobilized enzyme is not affected, if formation of multiple immobilization bonding is unavoidable under the given immobilization conditions. However, the two conditions described above are contradictory each other. In order to increase the number of the immobilized DNA polymerase, the concentration of the immobilization reaction group should be increased. In this case, however, the probability of forming a plurality of covalent bonding per immobilized DNA polymerase becomes high due to existence of too many immobilization reaction groups, and therefore the probability of losing the activity becomes high. In the opposite case where the concentration of the immobilization reaction group is too low, the number of covalent bonding for immobilization per immobilized DNA polymerase becomes low enough that the activity can be preserved. However, the number of the immobilized DNA polymerase decreases, and therefore the overall activity can be reduced. In the present invention, it is confirmed that the activity of the immobilized DNA polymerase increases and then decreases as the concentration of the reaction group for immobilization on the substrate material increases. It is therefore demonstrated that construction of an immobilized DNA polymerase with an optimized high activity can be possibly provided, by optimizing the two contradictory conditions.

In order to measure the activity of the immobilized DNA polymerase, PCR is performed with the immobilized DNA polymerase, and the result is compared with that obtained from the solution phase DNA polymerase wherein its amount corresponds to the maximum amount that can be immobilized on the substrate material. The average activity of the immobilized DNA polymerase was determined relative to that of the solution phase DNA polymerase. Since the immobilized DNA polymerase of the present invention is likely to be a mixture of DNA polymerases that are immobilized in a different manner, the activity of the immobilized DNA polymerase is given as the average activity relative to that of the solution phase DNA polymerase. The average activity of the immobilized DNA polymerase obtained in the present invention is more than about 10% relative to the maximum activity of the solution phase DNA polymerase, preferably more than about 20%, more preferably more than about 50% and sometimes as high as about 80% or more depending on the immobilization conditions. In addition, it is confirmed that the immobilized DNA polymerase can be recycled and reused after PCR.

As described above, the covalently immobilized DNA polymerase with highly preserved activity is realized in the present invention. At least in the case of the DNA polymerase, it is confirmed that there exists an immobilized state with the activity close to that of the solution phase DNA polymerase among various states of the immobilized DNA polymerase.

Because it is not quite possible with current technologies to precisely determine the structure of the immobilized DNA polymerase, it can be identified based on the activity change depending on the immobilization conditions.

The Taq DNA polymerase used in the embodiments of the present invention is a protein with molecular weight of 94 kD that is composed of 832 amino acids. When the immobilization reaction group of the linker is carboxyl as in the embodiments of the present invention, there exist in the Taq DNA polymerase 146 amino acids having primary amines that can react with the carboxyl to form amide bonding. Although there are a number of amino acids having primary amines located inside the Taq DNA polymerase, which cannot participate in immobilization reaction, the number of primary amines located outside the enzyme, which can form immobilization bonding, is estimated to reach several tens. Therefore, if the prior random immobilization takes place to nonspecifically form immobilization bonding, a plurality of covalent bonding can be formed at or near the active site. As a result, a possibility of losing the activity of the immobilized DNA polymerase becomes very high due to the structural change or damage in the active site. This expectation is confirmed from the results of the random immobilization performed as a control experiment in Example 4 of the present invention.

In the present invention, the immobilization reaction is performed with a DNA polymerase with its active site masked by a DNA substrate that binds to the active site of the DNA polymerase. Due to this masking, the immobilization takes place in an oriented manner since immobilization reaction at or near the active site is prevented. Even though the immobilization occurs at a site relatively distant from the active site by the oriented immobilization in the manner described above, a plurality of covalent bonding for immobilization can be formed to damage the activity of the immobilized DNA polymerase since a plurality of immobilization reaction groups that can participate in the immobilization reaction exist on the surface of the DNA polymerase. Therefore, in the present invention, the average number of immobilization bonding per immobilized DNA polymerase can be controlled, by changing the concentration of the immobilization reaction group of the linker on the substrate material formed.

As shown in Example 4, it is observed that the average activity of the immobilized DNA polymerase relative to that of the solution phase DNA polymerase reaches maximum when the concentration of the carboxyl group used as the immobilization reaction group on the substrate material is about 5%. This result can be interpreted as follows. The average activity of the immobilized DNA polymerase increases rapidly as the concentration of the carboxyl group on the substrate material increases from 0% to about 5%. This indicates that the number of immobilized DNA polymerases increases and the number of covalent bonding for immobilization per immobilized DNA polymerase is restricted to be one or as low as possible to preserve the activity.

The average activity of the immobilized DNA polymerase decreases rapidly as the concentration of the carboxyl group on the substrate material increases from about 5% to about 10%. This rapid decrease in the activity indicates that a considerable number of covalent bonding for immobilization are formed so that the activity of the immobilized DNA polymerase is damaged, even though the number of immobilized DNA polymerases increases.

Therefore, the structure of the most optimized immobilized DNA polymerase can be characterized in the following way.

For example, the immobilized DNA polymerase of the present invention forms covalent bonding not at or near the active site, but at a site relatively distant from the active site, leading to an immobilized structure that is oriented.

Also, the immobilized DNA polymerase provided in the present invention has a structure where the number of covalent bonding for immobilization per immobilized DNA polymerase is restricted to be one or as low as possible to avoid damaging the activity.

The conditions for constructing the immobilized DNA polymerase of the present invention are explained in more details below.

Firstly, the immobilized DNA polymerase of the present invention can be constructed by selecting a DNA polymerase from the group consisting of thermostable DNA polymerases such as the Taq DNA polymerase, its derivatives, and its mutants, and DNA polymerases that are not thermostable, such as the *E. coli* DNA polymerase, the T7 DNA polymerase, their derivatives, and their mutants. Most of these polymerases are commercially available or have been described in Maunders, M. J. (1993) In *Methods in Molecular Biology*, Ed. Burrell, M. M. (Humana Press, Inc., Totowa, N.J.), 16:17-30 Landgraf, A. and Wolfes, H. (1993) In *Methods in Molecular Biology*, Ed. Burrell, M. M. (Humana Press, Inc., Totowa, N.J.), 16:31-58. Totowa, N.J.), 16:31-58.

This is based on the fact that the DNA polymerases have similar structures and the same function. Broadly speaking, the DNA polymerase consists of two protein domains that are structurally separated. The two domains are also separated functionally because only one of the domains has the activity for DNA polymerization. In order for DNA polymerization to occur, a partially double stranded DNA should bind to the domain having the activity for DNA polymerization. The immobilized DNA polymerase of the present invention is constructed with an oriented immobilization that make it difficult to form covalent bonding for immobilization at the domain having the activity for DNA polymerization. This is because the active site of the DNA polymerase is masked with a partially double stranded DNA substrate. Thus, the immobilized DNA polymerase of the present invention is constructed by forming covalent bonding for immobilization mainly at the other domain that does not have the activity for DNA polymerization. It will be obvious to those skilled in the art that instead of the Taq DNA polymerase, other DNA polymerases that have similar structures and functions to those of the Taq DNA polymerase can be used to construct immobilized DNA polymerases that have highly preserved activity, with the same structural characteristics. Examples include catalytically active fragments of full-length polymerase enzymes.

Additionally, the immobilized DNA polymerase of the present invention can be constructed using various linkers that are characterized in having a reaction group at one end that is capable of binding to the DNA polymerase and a reaction group at another end that is capable of binding to the substrate material. In one embodiment of the present invention, 12-mercaptododecanoic acid, which has reaction groups at both ends of the 11 carbon chain, is used as a linker capable of binding to the DNA polymerase and the substrate material. However any material can be used if it has a reaction group at one end that is capable of binding to the DNA polymerase and a reaction group at another end that is capable of binding to the substrate material. It will be preferable to use a linker that has a sufficient length so that interactions can be minimized between the immobilized DNA polymerase and the surface of the substrate material or a matrix formed on the surface. Therefore, in addition to the linker having a single alkane chain less than about 50 carbon atoms in length as used in the embodiments of the present invention, a linker comprising unsaturated carbon bonding, nitrogen, oxygen, sulfur, phosphorus, etc. or a linker having branched chain structure can be used provided the linker has the same or similar length as the single alkane chain.

Additional acceptable linkers having these and other useful characteristics have been disclosed in this application including references cited herein. See also G. E. and Feeney, R. E. (1974) in *Chemical Modification of Proteins*, Holden-Day; and S. S. Wong (1991) in *Chemistry of Protein Conjugation and Cross-Linking*, CRC Press.

In addition, the substrate material of the immobilized DNA polymerase of the present invention can be selected from the group consisting of metal, nonmetal, metalloid, their compounds, and their mixtures. The substrate material can be constructed using a material having reaction groups or reaction sites capable of forming chemical bonding with a linker on its surface.

In the embodiments of the present invention, gold is used because immobilization conditions can be easily controlled. However, any substrate material can be used if it has reaction groups or reaction sites capable of forming chemical bonding with the linker on its surface.

Further, the immobilized DNA polymerase of the present invention can be constructed by forming covalent bonding between the DNA polymerase and the linker. It is particularly preferable to use amide bonding between primary amine and carboxyl groups, because they can react in mild conditions so as not to influence the enzyme structure. In general, proteins have various reaction groups such as amine, carboxyl, hydroxyl, imidazole, phenol, thiol, and indole. Therefore, the immobilization reaction can be selected by choosing a particular reaction group. However, it is preferable to select a reaction group that can react at a mild condition, compared to a reaction group whose reaction condition is so hard to affect the stability of the enzyme. Therefore, it is most preferable to use amide bond formation reaction between primary amine and carboxyl, which can occur at low temperature in aqueous solution. In the embodiments of the present invention, amide bond formation reaction between the primary amine of the DNA polymerase and the carboxyl of the linker was used. However, it is also possible to use the opposite case where the carboxyl of the DNA polymerase and the primary amine of the linker are chosen to react.

In addition, the immobilized DNA polymerase of the present invention is characterized in that a matrix molecule having a non-reactive terminal group binds to the substrate material in addition to the linker.

Any matrix molecule can be used if it does not hamper the stability of the DNA polymerase. In the embodiments of the present invention, the matrix molecule is used to control the concentration of the linker having the immobilization reaction group on the substrate material. More specifically, the concentration of the linker bound to the surface of the substrate material is controlled by changing the relative concentration of the matrix molecule. In addition to this function, it is possible to increase the activity preservation ratio or the stability of the DNA polymerase by selecting an appropriate matrix molecule. The influence of the matrix molecule is shown in the embodiments of the present invention by comparing the two cases where 6-mercapto-1-hexanol and 1-heptanethiol are used as matrix molecules.

Further provided by the present invention is a composition for performing one or multiple polymerase chain reactions (PCR). Preferably, the composition is reusable for more than one use e.g., two, three of four of such uses. In one embodiment, the composition includes at least one type of DNA polymerase or catalytically active fragment thereof (preferably one type of enzyme or fragment) bound to a substrate material through a reactive linker. Typically, the number density of the reactive linker is between from about $2 \times 10^{11}$ cm$^{-2}$ to about $2 \times 10^{14}$ cm$^{-2}$ and the immobilized DNA polymerase exhibiting at least about 10% of the activity of the corresponding DNA polymerase in solution.

Preferred matrix molecules, substrate materials, linkers, masking agents, DNA polymerases and fragments thereof, are disclosed above and in the following discussion and Examples.

The invention also provides a kit for performing the PCR methods disclosed herein.

Other and further objects, features and advantages of the invention will be apparent from the following description taken in connection with the accompanying drawing. In describing the present invention, detailed explanations will be omitted when the explanation on the related prior art can unnecessarily make the points of the present invention vague. Below, referring to the attached drawings, the preferred embodiments according to the present invention are explained in detail.

Figure 1:
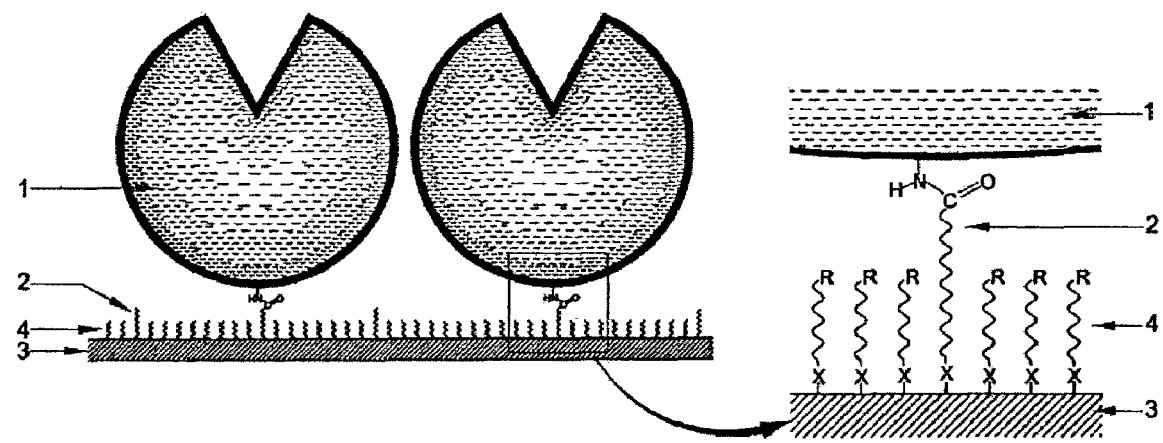
FIG. 1 is a diagram showing the construction of the immobilized DNA polymerase of the present invention.

The Drawings are better understood by reference to the following: 1: DNA polymerase, 2: linker, 3: substrate material, 4: matrix, and 5: DNA substrate.

The following examples are illustrative of the present invention. All references disclosed herein are incorporated by reference.

DETAILED DESCRIPTION OF THE INVENTION

As discussed, the present invention features a method for immobilizing at least one type of DNA polymerase or catalytically active fragment thereof to one or combination of substrate materials. More particularly, the invention relates to an efficient immobilization method that maximally preserves the catalytic activity of the immobilized DNA polymerase by masking the active site of the molecule and preferably reducing interaction of the masked molecule to the substrate material. The invention thus protects the active site and accessory (non-catalytic) sites of the DNA polymerase or fragment from undesired reaction with the substrate material.

As also discussed, practice of the invention is broadly applicable to the immobilization of a wide range of DNA polymerases and catalytically active fragments thereof. Reference herein to a "catalytically active" fragment of a particular DNA polymerase means that the fragment has at least about 70% of the activity of the full-length molecule as determined by a PCR assay as disclosed herein.

The invention is fully compatible with a variety of suitable substrate materials to which immobilization of one or a combination of different DNA polymerases and/or fragments is desired. Such substrate materials include those described already as well as a matrix of an affinity column, a synthetic or semi-synthetic carbohydrate, polymer, copolymer, graft co-polymer, polymer adduct, liposome, lipids, microparticle, microcapsule, emulsion or colloidal gold composition. Additionally suitable substrate materials include soluble synthetic polymers such as poly(ethylene glycol), poly(vinyl pyrrolidone), poly(vinyl alcohol), poly (amino acids), divinylether maleic anhydride, ethylene-maleic anhydride, N-(2-hydroxypropyl)methacrylamide, dextran; and blends thereof. See also the U.S. Pat. No. 6,172,202 and references cited therein for additionally suitable polymers. Also suitable for use with the invention are certain co-polymers, polymer blends, graft co-polymers and polymer adducts that are known to be useful for immobilizing biologically active molecules.

As mentioned previously, it is possible to control the rate of immobilization of the masked DNA polymerase to a desired substrate material by one or a combination of different strategies in accord with this invention. However, it will often be preferred to reduce the rate of immobilization by one or a few means such as by controlling the mole fraction (or the number density) and the reactivity of the reaction group on the substrate material. In embodiments in which the immobilization is to be carried out in an automated or semi-automated fashion (such as in the production of a slide, chip, filter or wafer with immobilized DNA polymerase), it will often be useful to control the rate of immobilization by controlling reactivity of one or more linkers bound to the substrate material.

Thus in one invention embodiment, a desired substrate material is contacted by mixture of linkers that includes at least one reactive linker and at least one nonreactive linker. By the phrase "reactive linker" is meant a polyvalent linking molecule such as has already been disclosed, for instance having two chemically reactive groups, in which one reactive chemical group is bound to the substrate material and another reactive (or reaction) group is generally free to bind to the masked molecule. A "non-reactive linker" is usually monovalent and can be substantially the same or even different from the reactive linker except that the non-reactive linker will not have a reactive group free to bind to the masked molecule. A preferred example of an unreactive linker according to the invention is a matrix molecule. Thus by contacting the substrate material with the linker mixture, it is possible to adjust the mole fraction of reactive and non-reactive linker (matrix molecule) and desirably control binding of the masked molecule to the substrate material. This feature of the invention allows the user (or an automated device under control of the user) to select the rate of immobilization of the masked molecule to the substrate material. As discussed, it has been found that by controlling the mole fraction (or the number density) of the reactive linker to between about 0.5% to about 50% (about $2 \times 10^{12}$ $cm^{-2}$ to about $2 \times 10^{14}$ $cm^{-2}$), preferably about 0.5% to about 30% (about $2 \times 10^{12}$ $cm^{-2}$ to about $1.2 \times 10^{14}$ $cm^{-2}$), more preferably about 0.5% to about 10% (about $2 \times 10^{12}$ $cm^{-2}$ to about $4 \times 10^{13}$ $cm^{-2}$), it is possible to maximize catalytic activity of the masked and immobilized DNA polymerase per unit area of the substrate material. Without wishing to be bound to theory, it is believed that by maintaining the mole fraction of the reactive linker within this preferred range and immobilizing a DNA polymerase whose active site is masked by a masking agent, it is possible to minimize harmful immobilization reaction to the active and non-catalytic accessory sites of the polymerase. Especially preferred reaction parameters provide for an average of less than about five, preferably less than about three and more preferably about one covalent bond per bound DNA polymerase.

By the phrase "controllably reacting", "reacting under controlled conditions" or related phrases is meant, went it is intended to refer to immobilization of a desired DNA polymerase or fragment to a substrate material, performing a reaction under conditions such that the mole fraction (or the number density) of the reaction group (e.g., as present on a linker) is between from about 0.5% to about 50% (about $2 \times 10^{12}$ $cm^{-2}$ to $2 \times 10^{14}$ $cm^{-2}$), preferably about 0.5% to about 30% (about $2 \times 10^{12}$ $cm^{31 \ 2}$ to about $1.2 \times 10^{14}$ $cm^{-2}$), more preferably about 0.5% to about 10% (about $2 \times 10^{12}$ $cm^{-2}$ to about $4 \times 10^{13}$ $cm^{-2}$). Typically preferred controlled reactions bind a masked and biologically active molecule of interest to less than about two or three suitable reactive groups, preferably about one of same.

Generally, a maximum of about 400 reaction groups can be introduced on about a 10 nm diameter area of the substrate such as Au. Therefore, if the size of the DNA polymerase to be immobilized is about 10 nm diameter which is similar to the size of the Taq DNA polymerase and most antibodies, an average of one reaction group will be available for each molecule at about 0.25% mole fraction. For smaller molecules, a higher percentage will be needed to provide average of one reaction group to each molecule, for instance, about 25% molecule fraction (or about $1 \times 10^{14}$ $cm^{-2}$ number density) for about 1 nm diameter molecule and about 1% mole fraction (or about $4 \times 10^{12}$ $cm^{-2}$ number density) for about 5 nm diameter molecule. Moreover, in many available reaction conditions (especially in aqueous solution), the reaction probability of the reaction group is substantially lower than 100%. Therefore, about 0.5% would be a reasonably lower limit that gives a wide enough range to practice most invention embodiments.

By the phrase "specific binding" or a related phrase is meant formation of a complex between two or more molecules, preferably two, that is essentially mutually exclusive as determined by standard binding tests including radioimmunoassay, gel assay, centrifugation sedimentation, Western blot, etc. Thus a masking agent in accord with the invention will "specifically bind" a biologically active molecule of interest if it forms a complex with that molecule and no other as determined by the standard binding tests.

In some embodiments, use of the non-reactive linker may not be necessary. That is, use of the reactive linker alone can also give desired results if the number density of the reactive linker (or the reaction group) on the support material is controlled to be within the preferred range described above, i.e., between about $2 \times 10^{12}$ $cm^{-2}$ to $2 \times 10^{14}$ $cm^{-2}$, preferably about $2 \times 10^{12}$ $cm^{-2}$ to about $1.2 \times 10^{14}$ $cm^{-2}$, more preferably about $2 \times 10^{12}$ $cm^{-2}$ to about $4 \times 10^{13}$ $cm^{-2}$.

In some other embodiments, the substrate material itself may already have the reactive linkers or the reaction groups with their number density controlled or maintained within the preferred range described above.

EXAMPLE 1

Preparation of the Immobilized DNA Polymerase According to the Present Invention—PIM (Protected Immobilization Method)

The 65 base single stranded DNA (ss-DNA) (SEQ ID NO: 1) and the KS primer (SEQ ID NO: 2) shown below was mixed in an aqueous buffer solution at 1:1 molar ratio, and the resulting solution was incubated for 10 minutes at 94° C. and was then cooled down slowly below 35° C. During this process, the 65 base ss-DNA (SEQ ID NO: 1) and the KS primer (SEQ ID NO: 2) were annealed to form a partially double stranded DNA. An appropriate number of moles of Taq DNA polymerase (AmpliTaq Gold) purchased from Perkin Elmer (U.S.A.) was then added to this solution and the resulting mixture was incubated in a dry bath at 72° C. for 10 minutes. After this, the mixture was moved to a dry bath at 50° C. and incubated for 20 minutes to prepare the PIM enzyme solution of the masked Taq DNA polymerase.

```
KS primer 5'-CGAGGTCGACGGTATCG-3'                              (SEQ ID NO:2)

65-mer    3'-CCAGCTGCCATAGCTATTTTCTTTTCTTTCTTAAGTTCT            (SEQ ID NO:1)

TTTCTTTTCCTAGGTGATCAAGATCT-5'
```

The Au substrate used was a glass plate of 3.0 mm×5.0 mm size on which Au was vacuum-deposited to about 1000 Å thickness. In order to ensure the cleanness of the surface of the Au thin film, it was washed with Piranha solution for about 10 to 15 minutes at about 60 to 70° C. right before using and was rinsed with deionized water and subsequently with absolute ethanol.

In order to introduce the immobilization reaction group on the Au surface, a monolayer of thiol molecules was formed on the Au surface by using the Au—S bond formation reaction, that is, by using the thiolate formation reaction between the linker having a thiol group and Au. At this time, the mixed solution of two kinds of thiol molecules having an immobilization reaction group and a non-reactive group was used. The mole fraction of thiol molecules having the immobilization reaction group was controlled by changing its mole fraction in the range of about 0 to about 100%, in. order to control the mole fraction of the immobilization reaction group on the substrate material. In order to introduce a carboxyl immobilization reaction group, 12-mercaptododecanoic acid with a relatively longer alkyl chain was used. As a thiol molecule having a non-reactive group, 6-mercapto-1-hexanol or 1-heptanethiol was used. The Au thin film was placed in 100 µl of a 2 mM mixed thiol solution in ethanol for 2 hours at room temperature to introduce the carboxyl immobilization reaction group, and it was washed with absolute ethanol.

The Au thin film where the carboxyl immobilization reaction group was introduced was placed in 120 µl of an ethanol solution containing 10 mM of 1-ethyl-3-(3-dimetylaminopropyl)carbodiimide (EDC) and 5 mM of N-hydroxysuccinimide (NHS) for 2 hours at room temperature to activate the carboxyl group. The carboxyl group reacts with NHS in the presence of EDC to form NHS-ester, thereby being activated.

After activating the carboxyl immobilization reaction group on the monolayer, the Au substrate was moved to the PIM enzyme solution. In this step, the activated carboxyl (NHS-ester) on the monolayer reacted with the primary amine (—$NH_2$) of the protein to form amide bond (—CO—NH—). As a result, the Taq DNA polymerase was immobilized on the substrate material. The immobilization reaction was carried out at different conditions by varying concentration of the DNA polymerase, pH, reaction time, reaction temperature, etc.

FIG. 1 is a diagram showing the construction of the immobilized DNA polymerase prepared according to the present example. The DNA polymerase 1 forms covalent bonding with the linker 2. In the present invention, the primary amine of the polymerase forms amide bonding with the carboxyl of the linker. The linker 2 is connected to the substrate material 3 via a Au—S chemical bonding. As in the present example, it can be constructed with or without introducing a matrix molecule 4 having a non-reactive group.

Figure 2:
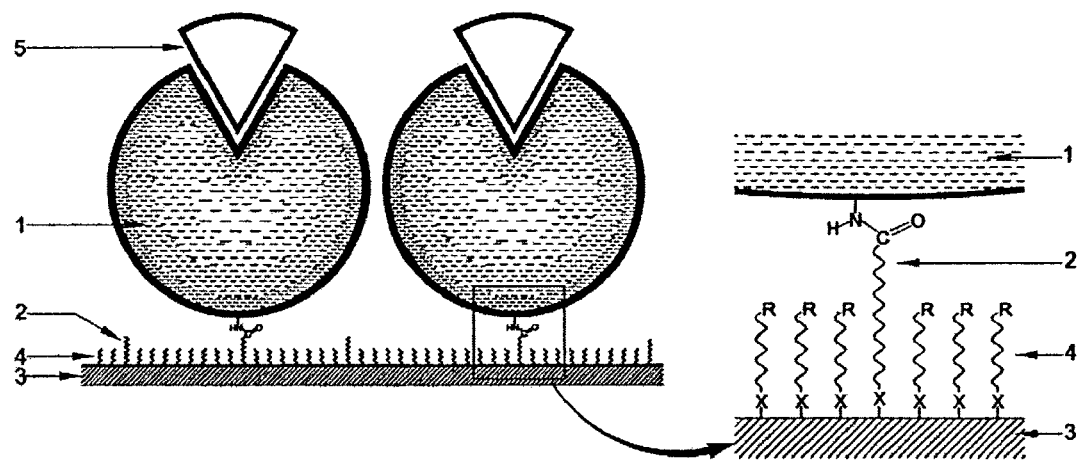
FIG. 2 is a diagram showing the construction of the immobilized DNA polymerase with the active site masked by a DNA substrate of the present invention.

FIG. 2 is a diagram showing the construction of the masked immobilized DNA polymerase prepared according to the present example. In this case, the DNA polymerase 1 binds to the linker 2 with its active site masked by a DNA substrate 5. The immobilized DNA polymerase shown in FIG. 1 in which the DNA substrate used to mask the active site is removed, can be prepared by performing polymerization reaction with the immobilized DNA polymerase in FIG. 2 in the presence of dNTP.

EXAMPLE 2

Preparation of the Immobilized DNA Polymerase by the Prior Method—RIM (Random Immobilization Method)

In this example, immobilization was performed by using a Taq DNA polymerase whose active site was not masked instead of the Taq DNA polymerase masked with the partially double stranded DNA substrate used in Example 1. The other immobilization processes and reaction conditions were the same as in Example 1. The activated Au substrate was placed in the RIM enzyme solution to prepare an immobilized DNA polymerase.

EXAMPLE 3

Measurement of the Activity of the Immobilized DNA Polymerase

In order to measure the activity of the immobilized DNA polymerases prepared according to the methods of Examples 1 and 2, PCR was carried out, and the amount of the resulting amplified DNA was quantified. PCR was carried out in the Model 480 PCR thermal cycler of Perkin Elmer. The 65 bp ss-DNA (SEQ ID NO: 1) shown in Example 1 was used as a template, and the KS primer (SEQ ID NO: 2) and the SK primer (3'-CTAGGTGATCAAGATCT-5') (SEQ ID NO: 3) were used as primers for PCR. The volume of the PCR solution used was 50 µl. 25 fmol of the 65 base ss-DNA (SEQ ID NO: 1), 10 pmol each of the KS primer (SEQ ID NO: 2) and the SK primer (SEQ ID NO: 3), and 1.0 nmol dNTP were added to the PCR solution. As a buffer solution, the pH 8.3, 10× buffer purchased from Perkin Elmer was used after diluting 10 times. The temperature cycle was set as follows:

Hot start step: 94° C., 10 minutes
PCR cycle (20-45 cycles): 94° C., 30 s; 50° C., 60 s; 72° C., 30 s For quantification of the DNA amplified by the PCR, 20 µl of the PCR solution was sampled and analyzed by agarose gel electrophoresis. The PCR products were then visualized by fluorescence from ethidium bromide staining and they are quantified with a densitometer.

EXAMPLE 4

Activity of the Immobilized Taq DNA Polymerase as a Function of the Mole Fraction of the Carboxyl Immobilization Reaction Group The immobilization reaction was carried out in a phosphate buffer at pH 8.3 for 30 minutes at 50° C. The immobilized Taq DNA polymerase was prepared according to Example 1 and 2 with 50 µl of the immobilization reaction solution containing 0.75 pmol of Taq DNA polymerase. In the case of the PIM in Example 1, 1.5 pmol of the DNA substrate for active site protection added to the immobilization reaction solution. 0.75 pmol of the Taq DNA polymerase corresponds to the amount that can form three monolayers on the area of 3 mm×5 mm of the Au substrate used. 12-mercaptododecanoic acid was used as the linker, 6-mercapto-1-hexanol having a non-reactive group was used as a matrix molecule. 35 cycles of PCR were carried out and the resulting activity was then measured.

Figure 3A:
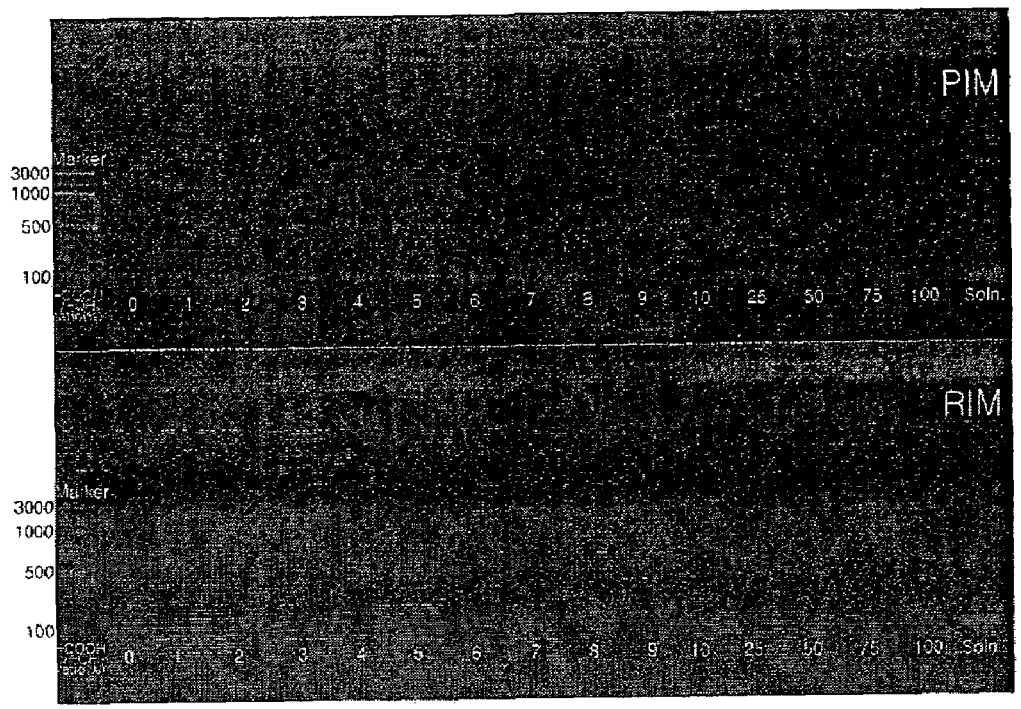
FIGS. 3a and 3b are agarose gel electrophoresis photographs and a graph comparing the immobilized DNA polymerases immobilized according to the present invention and the prior method.

FIG. 3a shows the agarose gel fluorescence photograph of the PCR products. The leftmost lane shows the ds-DNA molecular weight marker, and the rightmost lane shows the PCR product amplified with one monolayer amount of the solution phase Taq DNA polymerase. The other lanes show the PCR products amplified by using the immobilized Taq DNA polymerase. The numbers shown at the bottom are the mole fractions of 12-mercaptododecanoic acid relative to the total thiol molecules used for introducing the carboxyl group.

Figure 3B:
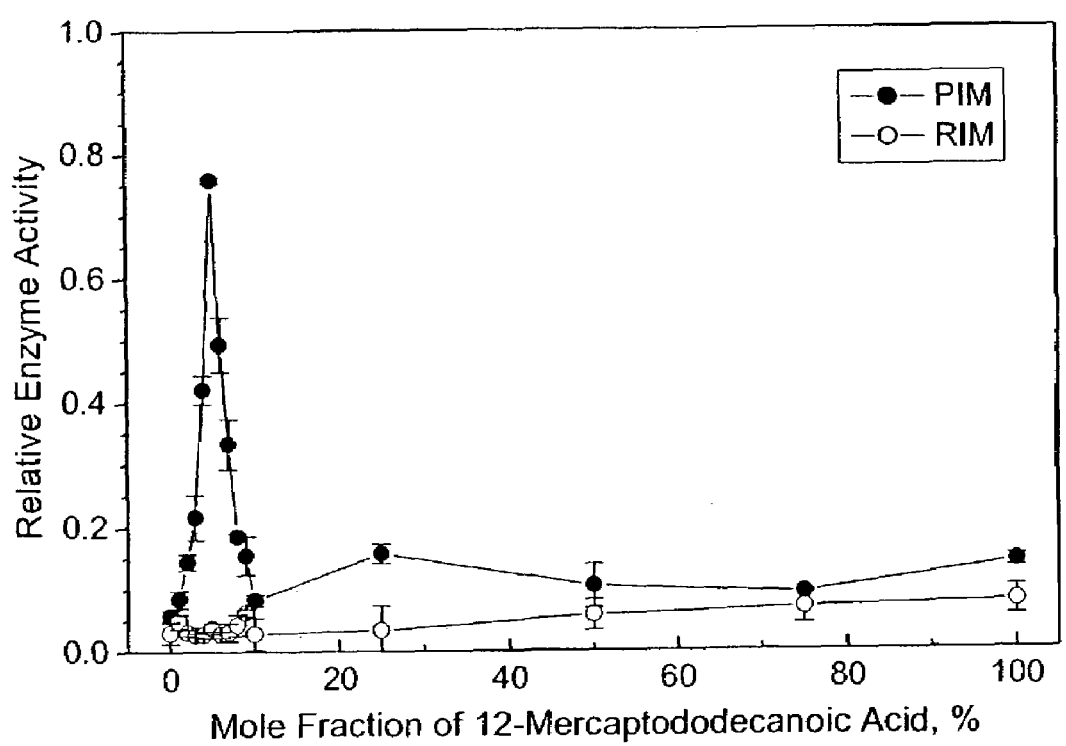

The activity determined from the agarose gel electrophoresis photographs in FIG. 3a is depicted in FIG. 3b. The abscissa is the mole fraction of the thiol molecule having the carboxyl group relative to the total moles of the thiol molecules used. The ordinate is the relative activity of the immobilized Taq DNA polymerase, as compared to the activity of one monolayer amount of the solution phase Taq DNA polymerase. As shown in FIGS. 3a and 3b, in the whole range of the mole fraction, the PIM with the active site masking in which oriented immobilization thus took place, shows higher activity than the RIM without the active site masking in which non-specific random immobilization took place. This demonstrates that the activity preservation of the PIM is much higher than that of the RIM because an oriented immobilization took place efficiently when the active site was masked.

The results in FIGS. 3a and 3b show that the activity of the immobilized DNA polymerase prepared by the PIM changes as the concentration of the caxrboxyl immobilization reaction group changes. The dramatic change occurs at the carboxyl concentration range of about 0 to about 10%. The average activity of the immobilized DNA polymerase increases rapidly as the concentration of the carboxyl group on the substrate material increases from 0% to about 5%. This indicates that the number of immobilized DNA polymerases increases and the number of covalent bonding for immobilization per immobilized DNA polymerase is restricted to be one or as low as possible to preserve the activity. The average activity of the immobilized DNA polymerase decreases rapidly as the concentration of the carboxyl group on the substrate material increases from about 5% to about 10%, although the number of immobilized DNA polymerases increases. This indicates that a considerable number of covalent bonding forms in most of the immobilized DNA polymerase, and thus the immobilized DNA polymerase is damaged, resulting in the reduction of the activity.

EXAMPLE 5

Activity of the Immobilized DNA Polymerase Depending on the Matrix Molecule

In order to confirm that the advantage of the present invention can be obtained when the matrix molecule is changed, the same method of the PIM as in Example 4 was used by changing the matrix molecule to 1-heptanethiol with the reaction time 90 minutes.

Figure 4A:
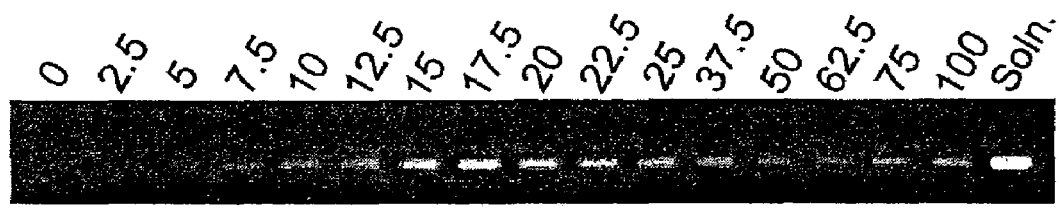
FIGS. 4a and 4b are an agarose gel electrophoresis photograph and a graph showing the activity change of the DNA polymerase depending on the characteristics of the matrix molecule.
Figure 4B:
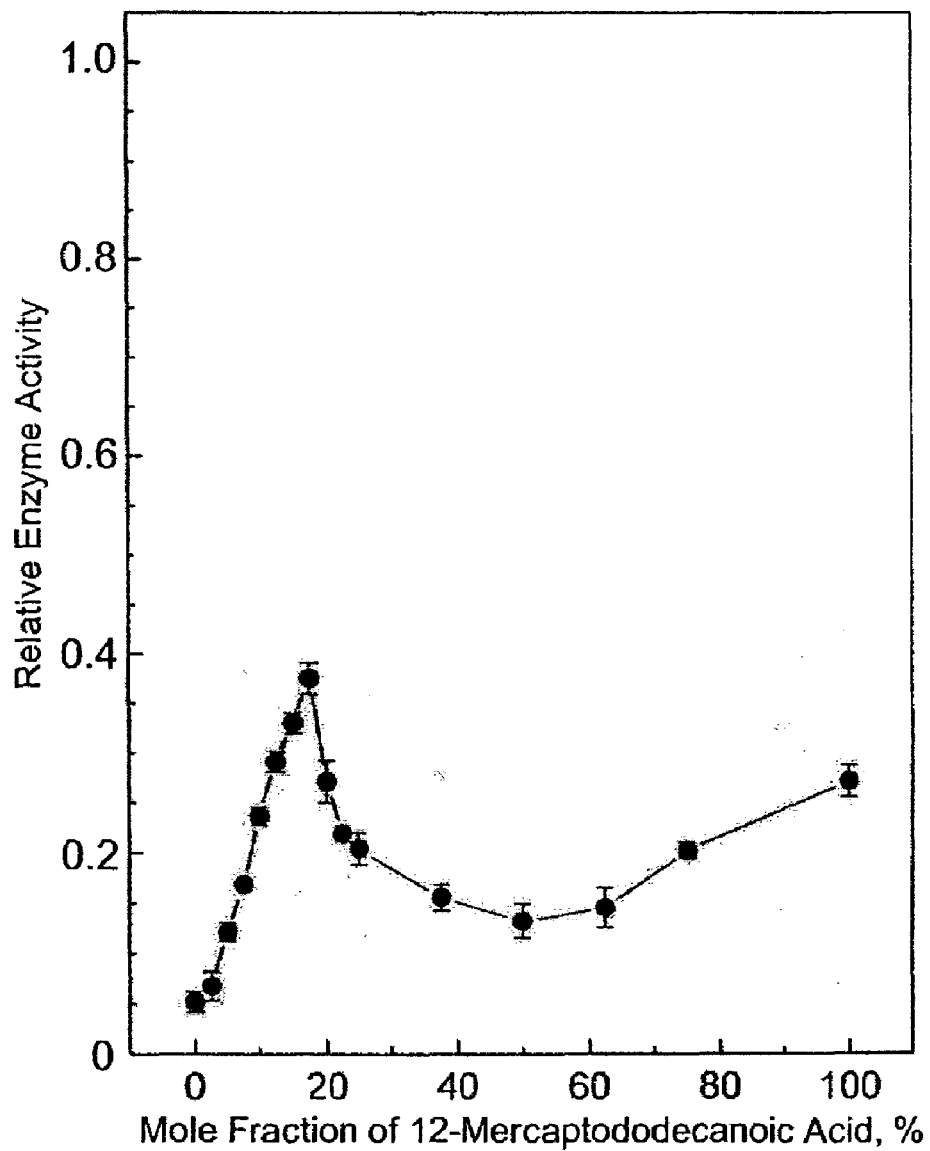

FIGS. 4a and 4b shows the results of the present example. The numbers shown at the bottom of FIG. 4a are the mole fraction of 12-mercaptododecanoic acid relative to the total number of thiol molecules used to introduce the carboxyl immobilization reaction group. As shown in the results, the activity is preserved above 10%, even though the matrix molecule is changed. Since the methyl non-reactive group introduced on the substrate material by 1-heptanethiol has physical and chemical properties that are different from the hydroxyl non-reactive group introduced by 6-mercapto-1-hexanol, the change of the activity observed as a function of the carboxyl mole fraction differs in the two cases.

EXAMPLE 6

Activity of the Immobilized DNA Polymerase as a Function of the Masking Ratio of the Active Site The number of moles of the partially double stranded DNA used to mask the active site relative to that of the Taq DNA polymerase used was varied from 0 to 2, and the activity of the immobilized Tag DNA polymerase was measured. The mole fraction of 12-mercaptododecanoic acid with respect to the total moles of the thiol molecules used for introducing the carboxyl immobilization reaction group on the Au surface was 5.0%. The total amount of the Taq DNA polymerase used for the immobilization reaction was 0.75 pmol, which corresponded to three monolayers. Other reaction conditions for immobilization and PCR were the same as in Example 4.

Figure 5A:
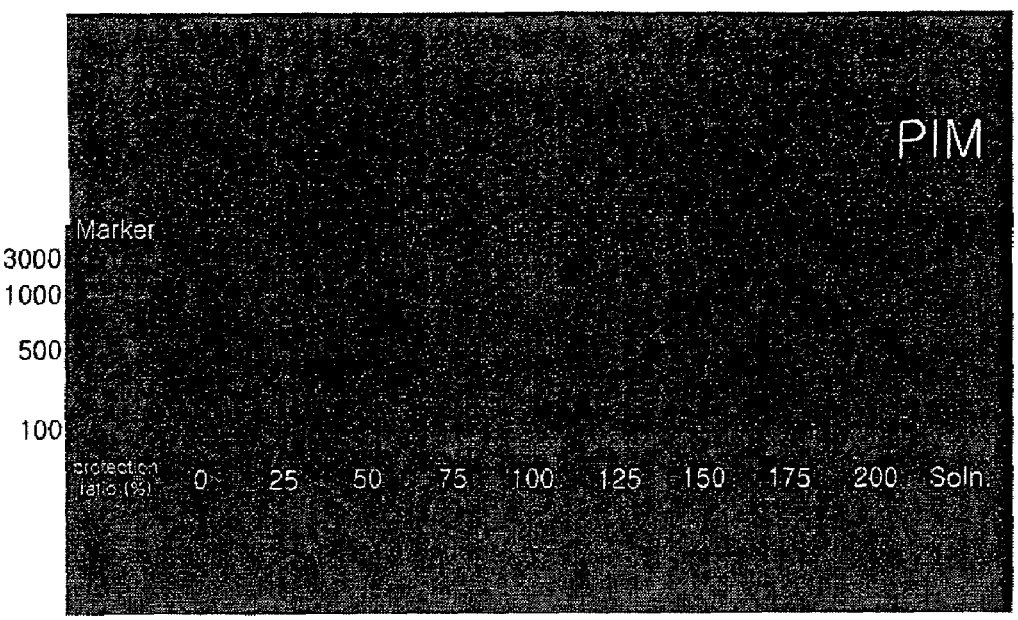
FIGS. 5a and 5b are an agarose gel electrophoresis photograph and a graph showing that the immobilization site of the immobilized DNA polymerase of the present invention is oriented due to the masking of the active site.
Figure 5B:
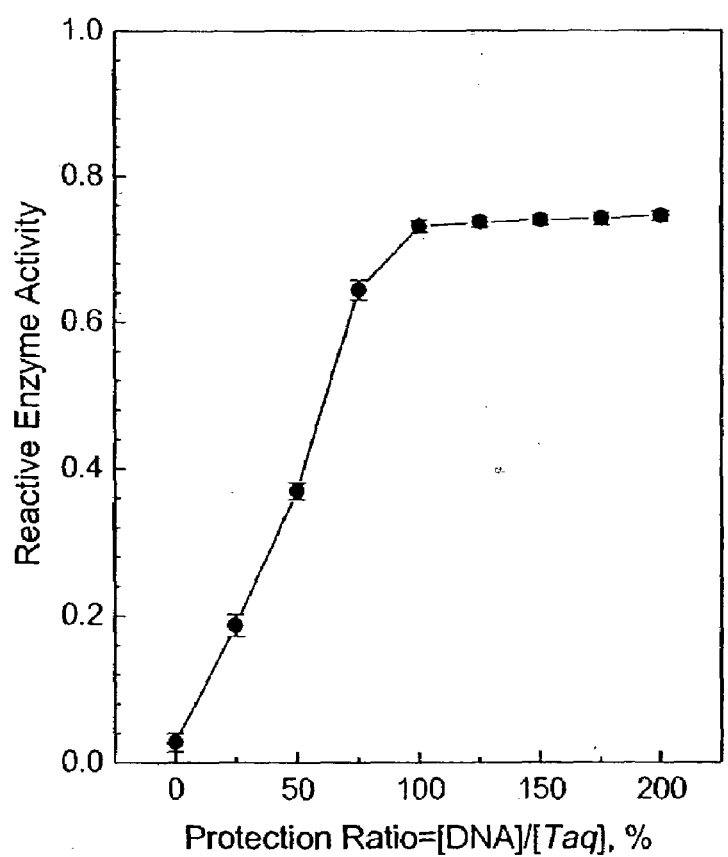

The results are shown in FIGS. 5a and 5b. The activity of the immobilized enzyme is shown as the relative enzyme activity compared to that in solution. In FIG. 5a, the leftmost and rightmost lanes are the same as in FIG. 3a, and the other lanes are the results of the PCR products amplified with the immobilized Taq DNA polymerases at different masking ratio. The numbers given at the bottom are the ratio corresponding to the number of moles of the partially double stranded DNA used for masking relative to that of the Taq DNA polymerase used. The activity of the immobilized DNA polymerase shown in FIGS. 5a and 5b increases until the active site masking ratio is 1.0, and at higher masking ratio it reaches a saturated state where no significant change is observed. This shows that the activity of the immobilized Taq DNA polymerase increases proportional to the masking ratio of the active site masked by the DNA substrate. It therefore demonstrates clearly that the activity of the immobilized enzyme can be preserved due to the oriented immobilization induced by the active site masking.

EXAMPLE 7

Activity of the Immobilized Taq DNA Polymerase in the PIM as a Function of the Immobilization pH In the present example, the activity of the immobilized DNA polymerase was measured at different immobilization pH, while keeping the mole fraction of 12-mercaptododecanoic acid at about 5.0% with respect to the total moles of the thiol molecules used for introducing the carboxyl immobilization reaction group on the Au surface. Other reaction conditions for immobilization and PCR were the same as in Example 4.

Figure 6A:
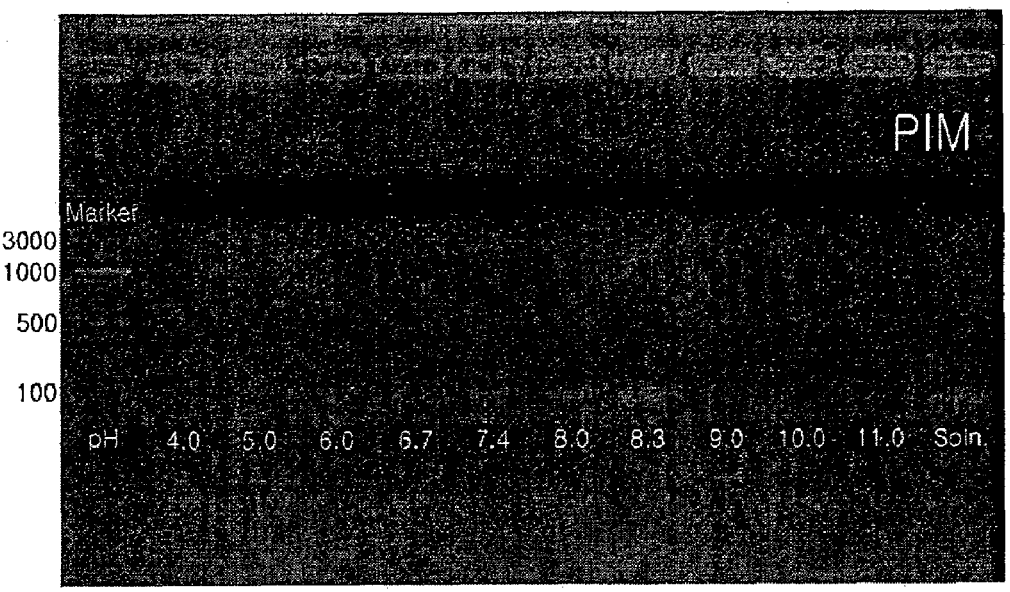
FIGS. 6a and 6b are an agarose gel electrophoresis photograph and a graph showing the activity change of the immobilized DNA polymerase depending on the pH of the reaction between the DNA polymerase and the linker in the process of preparing the immobilized DNA polymerase of the present invention.
Figure 6B:
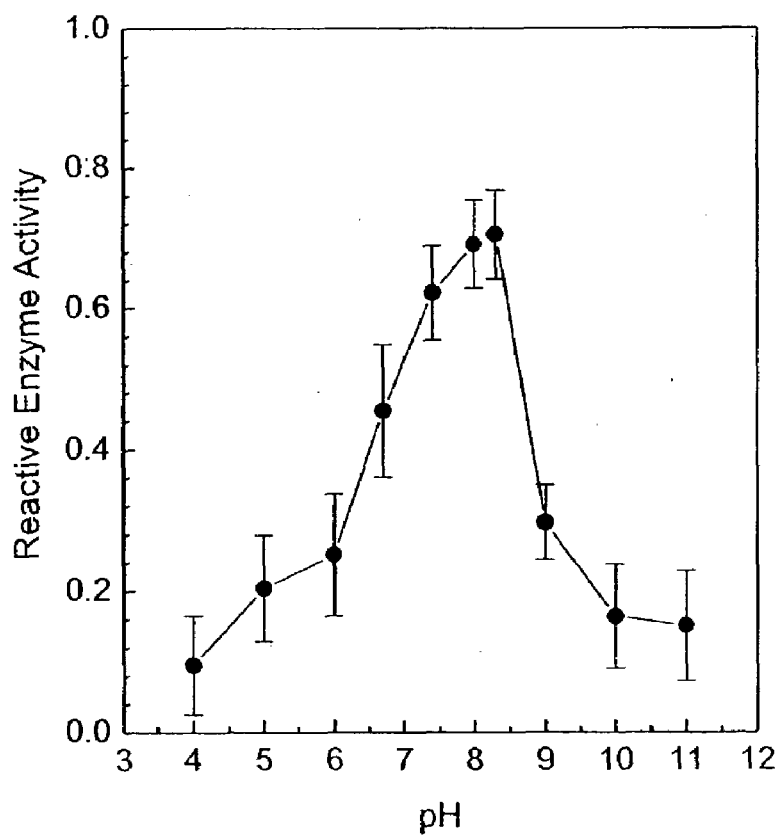

The results are shown in FIGS. 6a and 6b. The leftmost and rightmost lanes in FIG. 6a are the same as in FIG. 3a, and the other lanes are the results of the PCR products amplified with the immobilized Taq DNA polymerase at different pH shown at the bottom of each lane. FIGS. 6a and 6b show that the activity of the immobilized Taq DNA polymerase changes depending on pH. The activity of the immobilized Taq DNA polymerase is maximized at pH 8.3, where the binding activity of the Taq DNA polymerase is known to be maximum. This demonstrates again that the oriented immobilization induced by the active site masking is important for preserving the activity of the immobilized enzyme.

EXAMPLE 8

Comparison of the Activity of the Solution Phase and the Immobilized Taq DNA Polymerase Prepared by PIM as a Function of the Number of PCR Cycles The activity of the immobilized Taq DNA polymerase was measured at different number of PCR cycles, while keeping the mole fraction of 12-mercaptododecanoic acid at 5.0% with respect to the total moles of the thiol molecules used for introducing the carboxyl immobilization reaction group on the Au surface. Other reaction conditions for immobilization and PCR were the same as in Example 4.

Figure 7A:
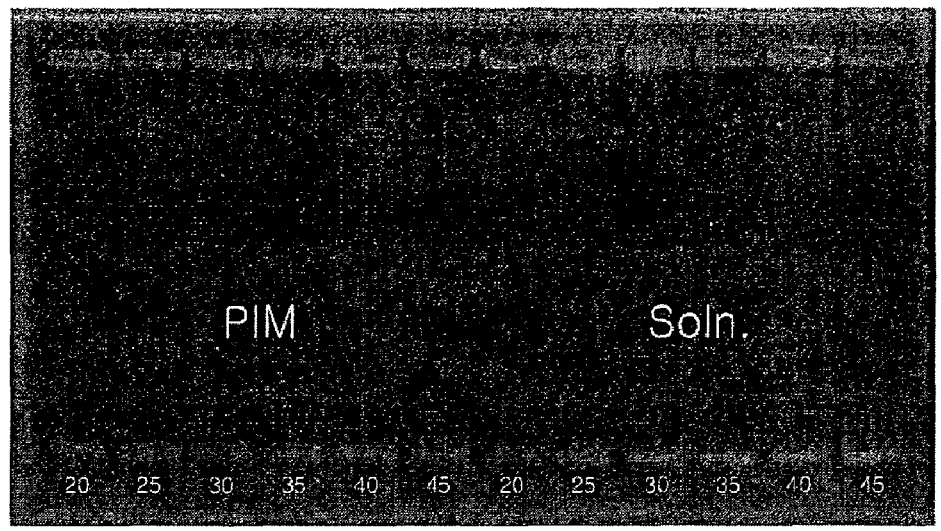
FIGS. 7a and 7b are an agarose gel electrophoresis photograph and a graph showing the efficiency of DNA amplification depending on the number of PCR cycles when the immobilized DNA polymerase of the present invention is used in PCR.
Figure 7B:
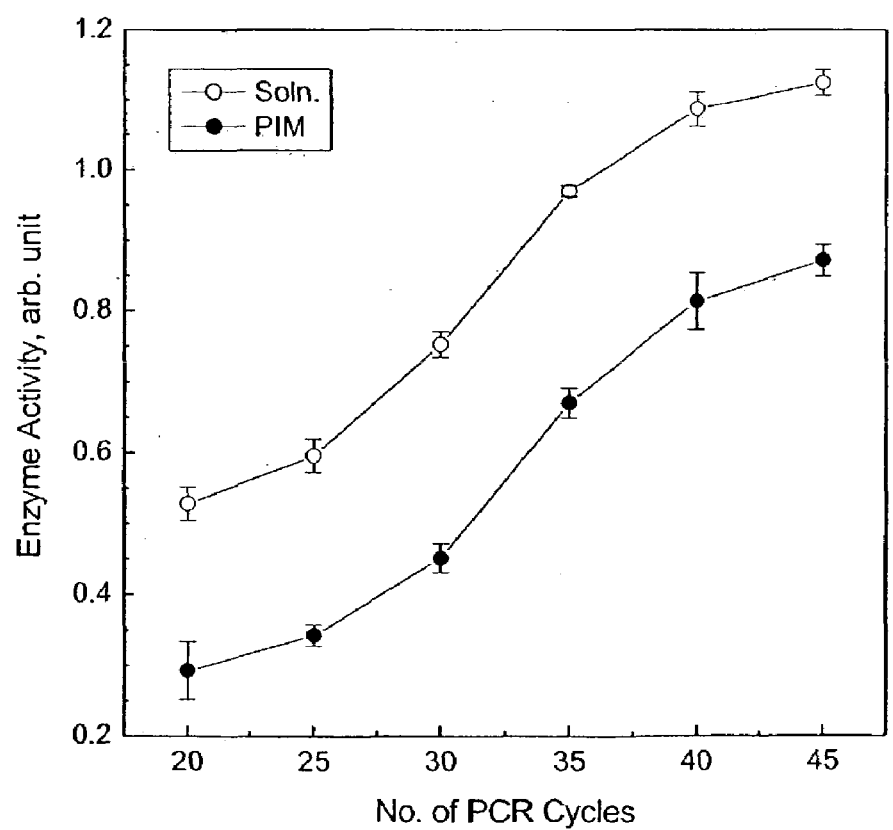

The results are shown in FIGS. 7a and 7b. In FIG. 7a, the number of PCR cycles is shown at the bottom of each lane. The trend observed in the activity of the immobilized Taq DNA polymerase is nearly identical to that of the solution phase Taq DNA polymerase. This suggests that the immobilized Taq DNA polymerase preserves its activity as in the solution phase.

EXAMPLE 9

Re-usage Experiment of the Immobilized DNA Polymerase Prepared by the PIM

Figure 8A:
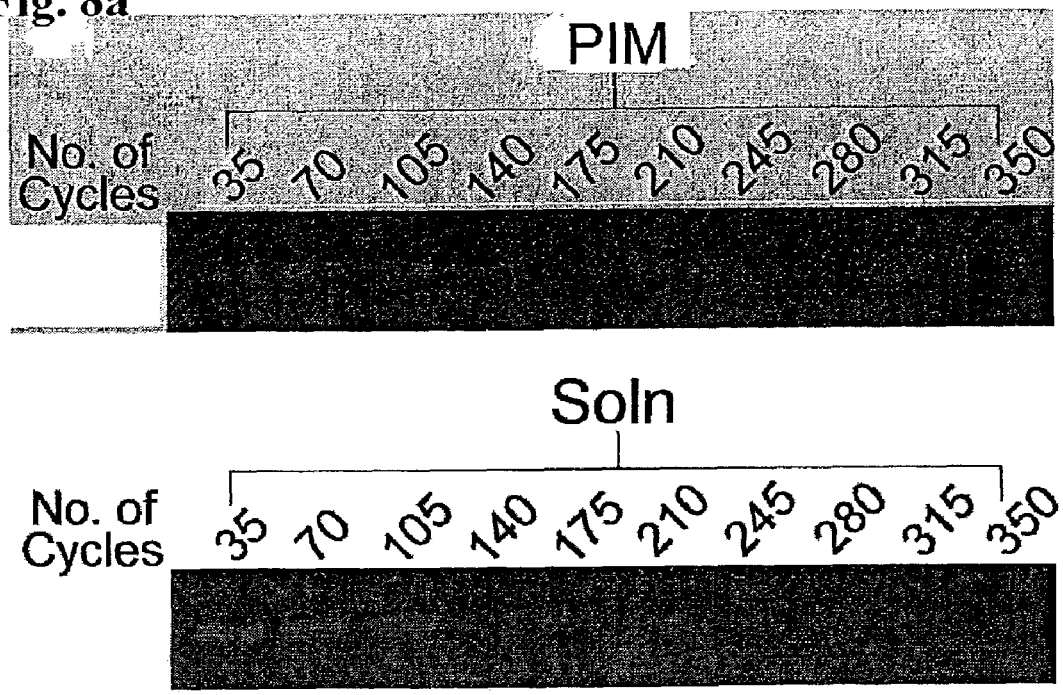
FIGS. 8a and 8b are agarose gel electrophoresis photographs and a graph showing the results when the immobilized DNA polymerase is reused.
Figure 8B:
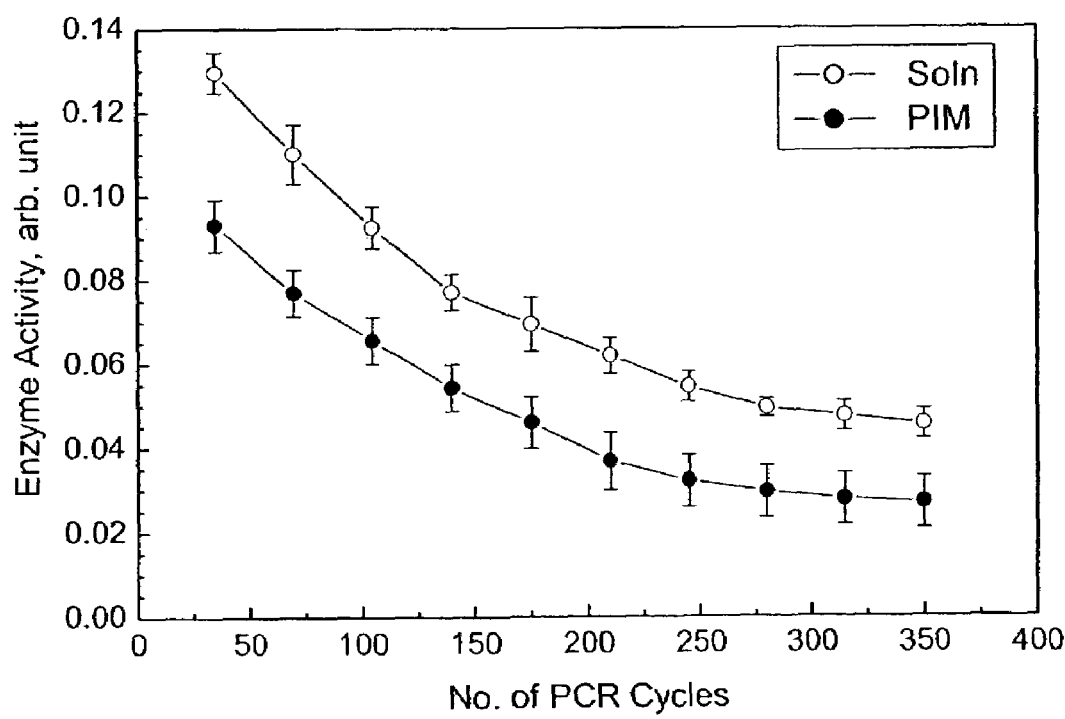

The mole fraction of 12-mercaptododecanoic acid with respect to the total moles of the thiol molecules used for introducing the carboxyl immobilization reaction group on the Au surface was kept at 5%, and all other reaction conditions for immobilization were the same as in Example 4. In order to observe the activity change when the immobilized Taq DNA polymerase is reused, the immobilized Taq DNA polymerase was taken out of the PCR tube after 35 cycles of PCR at the same conditions described at Example 3 and repeatedly used for new 35 cycles of PCR. The product of each PCR was analyzed. The results are shown in FIGS. 8a and 8b. The numbers shown above the agarose gel electrophoresis photograph in FIG. 8a are the numbers of the total PCR cycles.

In order to compare with change in the activity of the solution phase Taq DNA polymerase, a control experiment was performed as follows. The 35 cycles PCR was performed with the conditions described in Example 3. For the higher numbers of cycles, PCR was performed initially in the absence of dNTP and only the last 35 cycles were performed by adding dNTP. Since it is difficult to separate the solution phase Taq DNA polymerase with its activity preserved, new Taq DNA polymerase was used for each PCR reaction.

As shown in FIGS. 8a and 8b, the activity changes observed as a function of the number of PCR cycles show a similar pattern for both the solution phase and the immobilized Taq DNA polymerase prepared in the present example. In addition, it is shown that the immobilized DNA polymerase can be recycled and reused repeatedly. The observed reduction of the activity as the PCR cycles increase is due to the fact that the activity reduction of the Taq DNA polymerase is caused by the damage induced by heat at above 90° C. during the denaturation step in PCR. If the immobilized Taq DNA polymerase of the present invention is used in a polymerization reaction without a high temperature process, it can be reused for much more cycles.

EXAMPLE 10

Stability Test for Storage of the Immobilized DNA Polymerase Prepared by the PIM The mole fraction of 12-mercaptododecanoic acid with respect to the total moles of the thiol molecules used for introducing the carboxyl immobilization reaction group on the Au surface was kept at 5%, and all other reaction conditions for immobilization were the same as in Example 4. The immobilized Taq DNA polymerase was placed in a storage solution at 4° C. The storage solution was a 20 mM tris buffer at pH 9.0 containing 100 mM potassium chloride, 0.1 mM EDTA, 1.0 mM DTT (dithiothreitol), 0.5% Tween 20, and 50% glycerol. After each storage period, the activity of the immobilized Taq DNA polymerase was measured by performing 35 cycles of PCR as described in Example 3.

Figure 9A:
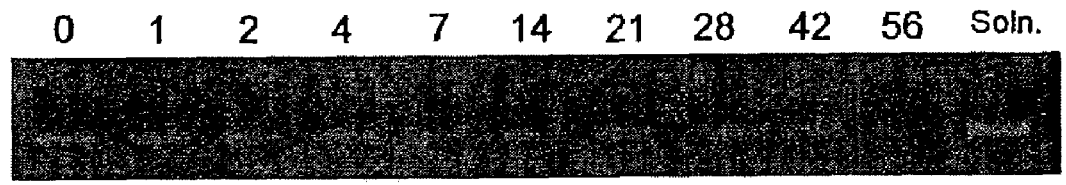
FIGS. 9a and 9b are an agarose gel electrophoresis photograph and a graph showing the stability of the immobilized DNA polymerase.
Figure 9B:
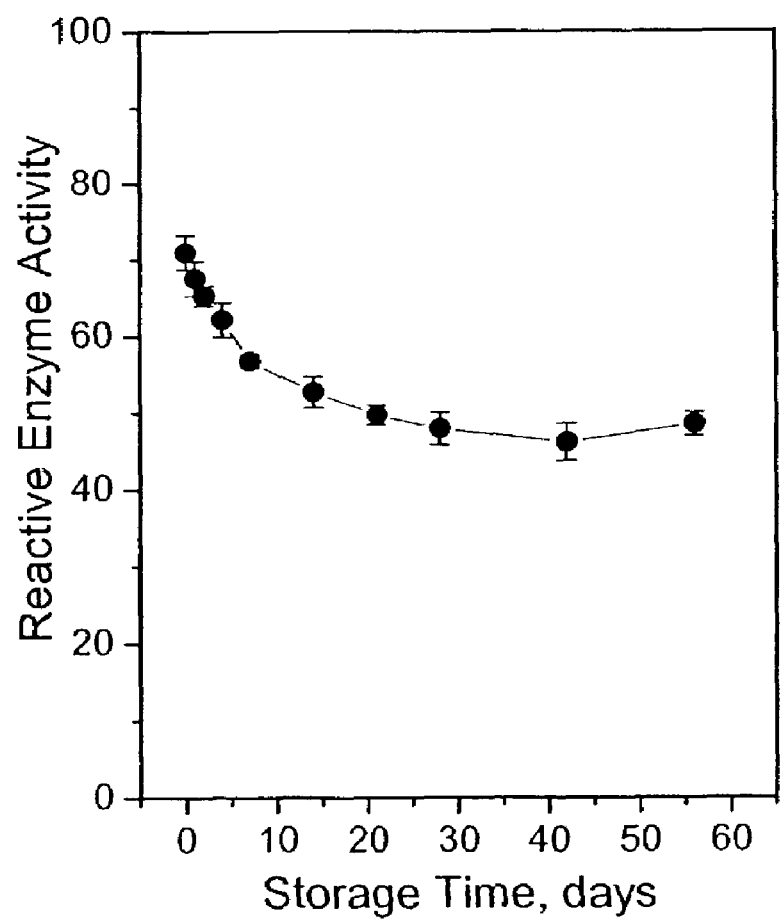

FIGS. 9a and 9b show the activity change of the immobilized Taq DNA polymerase depending on the storage period. The numbers shown at the upper side of FIG. 9a are storage periods. The results show that about 70% of the activity relative to the initial activity can be maintained even after the storage period of 2 month. This confirms that the immobilized DNA polymerase of the present invention is stable enough that it can be stored for a long period and reused.

Based on the drawings and the examples, it can be seen that the immobilized DNA polymerase of the present invention can preserve its activity from more than 10% to preferably 80%, under the conditions that the enzyme is immobilized with an oriented manner so as to form covalent bonding at a site other than the active site and also that the number of covalent bonding for immobilization is restricted to be one or an appropriate number to provide a desired structure for the immobilized enzyme.

As described above, since the present invention provides the immobilized DNA polymerase that is constructed to have highly preserved activity, separation and recycling of the DNA polymerase can be performed easily after the enzyme reaction. The immobilized DNA polymerase provided by the present invention thus make it possible to reuse the DNA polymerase and to simplify the purification process for the enzyme reaction sample. Therefore, it is possible to increase efficiencies of enzyme reaction processes and apparatuses in which the immobilized DNA polymerase that can simplify the separation process for the enzyme is used.

It should be further understood by those skilled in the art that many apparently different embodiments of this invention may be made without departing from the spirit and scope thereof. The present embodiment is therefore to be considered in all respects as illustrative and not restrictive. The scope of the invention being indicated by the appended claims rather than by the foregoing description and all changes which come within the meaning and range of equivalency of the claims are therefore intended to be embraced therein.

All references disclosed herein are incorporated by reference. In particular, co-pending application Ser. No. 10/406,155 by Hwang, Hyun Jin and Kim, Jeong Hee entitled "A Method For Immobilizing Biologically Active Molecules" as filed on Apr. 2, 2003 is specifically incorporated by reference.

What is claimed is:

1. An immobilized DNA polymerase comprising a DNA polymerase having an active site and an immobilization site, the immobilized DNA polymerase further comprising a linker, a matrix molecule, and a substrate material, wherein
    the DNA polymerase is bonded by a covalent bond with to the linker;
    the linker is bonded by a chemical bond to the substrate material;
    the immobilization site of the DNA polymerase is distant from the active site;
    the matrix molecule comprises a non-reactive terminal group and is connected to the substrate material together with the linker,
    and wherein the average number of covalent bonds formed between the immobilized DNA polymerase and the linker is such that average activity of the immobilized DNA polymerase is more than about 10% of the activity of solution phase DNA polymerase.

2. An immobilized DNA polymerase comprising a DNA polymerase having an active site and an immobilization site, the immobilized DNA polymerase further comprising a linker, a matrix molecule, and a substrate material, wherein
    the active site is masked with a DNA polymerase substrate;
    the DNA polymerase is bonded by a covalent bond with to the linker;
    the linker is bonded by a chemical bond to the substrate material;
    the immobilization site of the DNA polymerase is distant from the active site;

the matrix molecule comprises a non-reactive terminal group and is connected to the substrate material together with the linker,
and wherein the average number of covalent bonds formed between the immobilized DNA polymerase and the linker is less than about five bonds, such that average activity of the immobilized DNA polymerase after demasking is more than about 10% of the activity of solution phase DNA polymerase.

3. An immobilized DNA polymerase as in claim 1 or 2, wherein the DNA polymerase is a thermostable DNA polymerase or is a DNA polymerase that is not thermostable.

4. An immobilized DNA polymerase as in claim 1 or 2, wherein the linker comprises a reaction group at one end that is capable of binding to the DNA polymerase and a reaction group at another end that is capable of binding to the substrate material.

5. An immobilized DNA polymerase as in claim 1 or 2, wherein the substrate material is selected from the group consisting of metal, nonmetal, metalloid, compounds thereof, and mixtures thereof, and has reaction groups capable of forming chemical bonds with the linker on its surface.

6. An immobilized DNA polymerase as in claim 1 or 2, wherein the covalent bond between the DNA polymerase and the linker is an amide bond between a primary amine and a carboxyl group.

7. The immobilized DNA polymerase of claim 1 or 2, wherein the mole fraction of the linker relative to the total moles of the linker and the matrix molecule is between from about 0.5% to about 50%.

8. The immobilized DNA polymerase of claim 7, wherein the mole fraction of the linker relative to the total moles of the linker and the matrix molecule is between 0.5% to about 10%.

9. The immobilized DNA polymerase of claim 1 or 2, wherein the substrate material is a filter, polymer, co-polymer, polymer blend, graft co-polymer or polymer adduct.

10. The immobilized DNA polymerase of claim 9, wherein the substrate material is selected from the group consisting of poly(ethylene glycol), poly(vinyl pyrrolidone), poly(vinyl alcohol), poly(amino acids), divinylether maleic anhydride, ethylene-maleic anhydride, N-(2-hydroxypropyl) methacrylamide, dextran and a blend thereof.

11. The immobilized DNA polymerase of claim 2, wherein the average number of the covalent bonds formed between the immobilized DNA polymerase and the linker is less than about three.

12. The immobilized DNA polymerase of claim 2, wherein the average number of the covalent bonds formed between the immobilized DNA polymerase and the linker is about one.

13. The immobilized DNA polymerase of claim 1 or 2, wherein the number of the covalent bonds formed between the immobilized DNA polymerase and the linker is controlled by adjusting the number density of the linker on the substrate to between about $2\times10^{12}$ cm$^{-2}$ to $2\times10^{14}$ cm$^{-2}$.

14. The immobilized DNA polymerase of claim 3, wherein the thermostable DNA polymerase is a Taq DNA polymerase or catalytically active fragments or derivatives thereof.

15. The immobilized DNA polymerase of claim 3, wherein the DNA polymerase that is not thermostable is an *E. coli* DNA polymerase or a T7 DNA polymerase or catalytically active fragments or derivatives thereof.

16. The immobilized DNA polymerase of claim 1 or 2, wherein the DNA polymerase comprises two domains and one domain does not have polymerase activity, wherein the immobilization site of the DNA polymerase is present in the domain that does not have polymerase activity.

\* \* \* \* \*

UNITED STATES PATENT AND TRADEMARK OFFICE
CERTIFICATE OF CORRECTION

| | |
|---|---|
| PATENT NO. | : 7,238,505 B2 |
| APPLICATION NO. | : 10/406154 |
| DATED | : July 3, 2007 |
| INVENTOR(S) | : Hyun Jin Hwang and Jeong Hee Kim |

Page 1 of 1

It is certified that error appears in the above-identified patent and that said Letters Patent is hereby corrected as shown below:

Column 23, Line 57-58, "with to" should be changed to -- to --

Column 24, Line 62-63, "with to" should be changed to -- to --

Signed and Sealed this

Twenty Second Day of April, 2008

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 65
<212> TYPE: DNA
<213> ORGANISM: Artificial
<220> FEATURE:
<223> OTHER INFORMATION: Synthetic sequence
<220> FEATURE:
<221> NAME/KEY: misc_feature
<222> LOCATION: (52)..(65)
<223> OTHER INFORMATION: The nuclotides from 52 to 65 can be hybridized
      with KS primer of SEQ ID NO: 2 to form a partially double
      stranded structure.

<400> SEQUENCE: 1
tctagaacta gtggatcctt ttcttttctt gaattctttc ttttctttta tcgataccgt    60
cgacc                                                                65

<210> SEQ ID NO 2
<211> LENGTH: 17
<212> TYPE: DNA
<213> ORGANISM: Artificial
<220> FEATURE:
<223> OTHER INFORMATION: Synthetic sequence
<220> FEATURE:
<221> NAME/KEY: misc_feature
<222> LOCATION: (4)..(17)
<223> OTHER INFORMATION: PCR primer. The nuclotides from 4 to 17 can be
      hybridized with 65 bp ss-DNA of SEQ ID NO: 1 to form a partially
      double stranded structure.

<400> SEQUENCE: 2
cgaggtcgac ggtatcg                                                   17

<210> SEQ ID NO 3
<211> LENGTH: 17
<212> TYPE: DNA
<213> ORGANISM: Artificial
<220> FEATURE:
<223> OTHER INFORMATION: Synthetic sequence
<220> FEATURE:
<221> NAME/KEY: misc_feature
<222> LOCATION: (1)..(17)
<223> OTHER INFORMATION: PCR primer

<400> SEQUENCE: 3
tctagaacta gtggatc                                                   17
```